United States Patent [19]
Baumann et al.

[11] Patent Number: 5,836,987
[45] Date of Patent: Nov. 17, 1998

[54] APPARATUS AND METHOD FOR OPTIMIZING CARDIAC PERFORMANCE BY DETERMINING THE OPTIMAL TIMING INTERVAL FROM AN ACCELEROMETER SIGNAL

[75] Inventors: Lawrence S. Baumann, Bloomington; Bruce A. Tockman, Scandia; Rodney W. Salo, Fridley; Emanuel H. Silvermint, Shoreview, all of Minn.

[73] Assignee: Cardiac Pacemakers, Inc., St. Paul, Minn.

[21] Appl. No.: 815,697

[22] Filed: Mar. 12, 1997

Related U.S. Application Data

[63] Continuation-in-part of Ser. No. 558,837, Nov. 15, 1995, abandoned.

[51] Int. Cl.$^6$ .................................................. A61N 1/365
[52] U.S. Cl. ............................................. 607/17; 607/18
[58] Field of Search ................................. 607/17, 18, 24, 607/25

[56] References Cited

U.S. PATENT DOCUMENTS

| | | |
|---|---|---|
| 4,303,075 | 12/1981 | Heilman et al. . |
| 4,674,518 | 6/1987 | Salo . |
| 4,686,987 | 8/1987 | Salo et al. . |
| 4,922,930 | 5/1990 | Adkins et al. ............................ 607/19 |
| 5,024,222 | 6/1991 | Thacker . |
| 5,031,614 | 7/1991 | Alt ............................................. 607/18 |
| 5,063,927 | 11/1991 | Webb et al. ............................... 607/18 |
| 5,197,489 | 3/1993 | Conlan . |
| 5,334,222 | 8/1994 | Salo et al. ................................. 607/17 |
| 5,360,436 | 11/1994 | Alt et al. ................................... 607/18 |
| 5,476,483 | 12/1995 | Bornzin et al. ........................... 607/17 |
| 5,480,412 | 1/1996 | Mouchawar et al. ...................... 607/6 |
| 5,496,361 | 3/1996 | Moberg et al. . |
| 5,549,650 | 8/1996 | Bornzin et al. ........................... 607/24 |
| 5,554,177 | 9/1996 | Kieval et al. ............................. 607/17 |
| 5,674,256 | 10/1997 | Carlson ..................................... 607/17 |

OTHER PUBLICATIONS

James A. Ronan Jr., M.D., "Cardiac Auscultation: The First and Second Heart Sounds," *Heart Disease and Stroke*, May/Jun. 1992, pp. 113–116.

Margarete Hochleitner, M.D., Helmut Hortnagl, M.D., Choi–Keung Ng, M.D., Heidi Hortnagl, M.D., Franz Gschnitzer, M.D., and Wolfgang Aechmann, M.D., Cardiomyopathy, "Usefulness of Physiologic Dual–Chamber Pacing in Drug–Resistant Idiopathic Dilated Cardiomyopathy", *The American Journal of Cardiology*, 1990, vol. 66, pp. 198–202.

(List continued on next page.)

*Primary Examiner*—William E. Kamm
*Assistant Examiner*—George R. Evanisko
*Attorney, Agent, or Firm*—Haugen & Nikolai, PA

[57] ABSTRACT

A cardiac stimulating apparatus and method which optimizes cardiac performance by determining, from a filtered waveform transmitted from an accelerometer contained within the cardiac pacer, an optimum timing interval between at least one of intrinsic and paced stimulations of pre-selected chambers of the heart. Digitized data of the accelerometer signal, corresponding with identified R—R intervals, are stored for a plurality of preselected timing intervals for analysis and comparison. The accelerometer signal is filtered to isolate features of the waveform associated with specific cardiac events including for example, the first heart sound, the second heart sound or an amplitude in the frequency domain thereof. Characteristic values of these features of the accelerometer signal are calculated over a plurality of complete R—R intervals for each of the preselected timing intervals. The characteristic values are analyzed and compared to determine which timing interval optimizes cardiac performance. The cardiac stimulating apparatus and method may be used in any of several pacing modes including A-V pacing, V—V pacing, or A—A pacing.

20 Claims, 8 Drawing Sheets

OTHER PUBLICATIONS

Margarete Hochleitern, M.D., Helmut Hortnagl, M.D., Heide Hortnagl, M.D., Leo Fridrich, M.D., and Franz Gschnitzer, M.D., "Long–Term Efficiency of Physiologic Dual–Chamber Pacing in the Treatment of End–Stage Idiopathic Dilated Cardiomyopathy," *The American Journal of Cardiology*, vol. 70, Nov. 15, 1992, pp. 1320–1325.

Rick A. Nishimura, M.D., FACC, David L. Hayes, M.D., FACC, David R. Holmes, Jr., M.D., FACC, A. Jamil Tajik, M.D., FACC "Mechanism of Hemodynamic Improvement by Dual–Chamber Pacing for Severe Left Ventricular Dysfunction: An Acute Doppler and Catherterization Hemodynamic Study" *Journal of American College of Cardiology*, vol. 25, No. 2, Feb. 1995, pp. 281–288.

David Dra Mehta, Susan Gilmour, David E. Ward, A. John Camm, "Optimal Atrioventricular Delay at Rest and During Exercise in Patients with Dual Chamber Pacemakers: A Non–Invasive Assessment by Continuous Wave Doppler," *Br Heart J.*, 1989; vol. 61, pp. 16–166.

$<f_2>/<f_1>$

A-Vdelay interval $<f_2> * <f_1>$

A-Vdelay interval

APPARATUS AND METHOD FOR OPTIMIZING CARDIAC PERFORMANCE BY DETERMINING THE OPTIMAL TIMING INTERVAL FROM AN ACCELEROMETER SIGNAL

This application is a continuation-in-part of application Ser. No. 08/558,837, filed Nov. 15, 1995, now abandoned and entitled APPARATUS AND METHOD FOR OPTIMIZING CARDIAC PERFORMANCE BY DETERMINING THE OPTIMAL PACING INTERVAL FROM AN ACCELEROMETER SIGNAL AND AUTOMATICALLY ADJUSTING ACCORDINGLY FOR USE IN BRADY, TACHY AND CHF THERAPY DEVICES.

BACKGROUND OF THE INVENTION

I. FIELD OF THE INVENTION

This invention relates generally to an implantable, programmable, cardiac stimulating apparatus and method for optimizing cardiac performance. More particularly, the apparatus and method determines, from a filtered waveform transmitted from an accelerometer contained within the cardiac stimulating apparatus, an optimal timing interval between intrinsic or paced stimulations of pre-selected chambers of the patient's heart. The optimal timing interval is automatically or manually adjusted and may be determined for any of several preselected pacing modes.

II. DISCUSSION OF THE RELATED ART

The beneficial effects of dual-chamber (DDD) pacing on critically ill patients suffering from chronic heart failure (CHF) is described by Margarette Hochleitner et al. in a paper entitled "Usefulness of Physiologic Dual-Chamber Pacing in Drug-Resistant Idiopathic Dilated Cardiomyopathy" (*Am J Cardiol* 1990; 66:198–202). The patients involved in the underlying study were treated by implanting a DDD cardiac pacemaker whose atrial electrode was positioned near the right auricle and the ventricular electrode was positioned in the apical region of the right ventricle. The implanted pacemaker was programmed to have an atrioventricular (A-V) interval of 100 ms when pacing in the DDD mode. The 100 ms A-V interval was chosen as that offering the shortest possible delay that did not significantly impair cardiac function. The cardiac function was evaluated through echocardiographic studies and then the pacemaker was manually programmed to function with an A-V delay of 100 ms as a compromise between a shorter value that resulted in poor right ventricular compliance and a larger value that failed to show any significant improvement in cardiac function. The Hochleitner paper describes in detail the marked improvement in cardiac performance of the CHF patients due to the DDD pacing at the 100 ms A-V delay interval.

Patients exhibiting CHF typically have a very narrow range for the optimum A-V delay, meaning that small deviations, e.g., only 10 ms, from the optimum can diminish the clinical benefit obtained using DDD pacing. Thus, arbitrarily setting the A-V delay at a fixed programmed value as set out in the Hochleitner paper, may not guarantee the optimum benefit obtainable to the CHF patient population using DDD pacing. Thus, there is a need for a programmable cardiac stimulating apparatus that uses an adaptive approach to determine and adjust a timing interval, such as the A-V delay that is optimal.

In a recent paper entitled "Mechanism of Hemodynamic Improvement by Dual Chamber Pacing for Severe Left Ventricular Dysfunction: An Acute Doppler and Catheterization Hemodynamic Study" *JACC* vol 25, No.2, Feb. 1995 281–288), Nishimura et al. evaluated the acute effects of altering the A-V delay in heart failure patients by examining hemodynamic and Doppler indices collected during the A-V changes. They concluded that: 1) the A-V delay that provides optimal cardiac performance varies from patient to patient because of differences between patient's interatrial conduction, and 2) the time from atrial contraction to left ventricular contraction, a mechanical event not an electrical event, is important for ventricular filling. The interatrial conduction delays vary from patient to patient. Hence, advocating the programming of the same electrical A-V timing delay or interval for a group of patients as Hochleitner did is not altogether appropriate. What needs to be optimized then is the actual or true mechanical delay time or timing interval from atrial to ventricular contraction, for example, not the programmed electrical A-V delay. Therefore, there is a need for a device that analyzes a parameter that reflects mechanical events of the heart as well as the electrical events.

In accordance with the present invention, such a cardiac performance parameter can be obtained from an internally or externally mounted accelerometer sensor transmitting a filtered waveform which provides a means of monitoring the mechanical movements of the heart muscle, its valves, and the blood being pumped by it. In a review paper entitled "Cardiac Auscultation: The First and Second Heart Sounds" (*Heart Disease and Stroke,* 1992; 1:113–116), Ronan states that contractility, as defined by the peak dp/dt in left ventricular pressure at the time of mitral valve closure, is directly related to the amplitude of the $S_1$ or first heart sound. In addition, the intensity of the $S_1$ is influenced by the time interval between atrial and ventricular contraction.

In U.S. Pat. No. 5,549,650 issued to Bornzin et al. a device is described for providing hemodynamically optimal pacing therapy. The rate of pacing therapy is controlled by the Bornzin et al. device. In the Bornzin et al. device, an accelerometer sensor secured to an external portion of a patient's heart is used to derive cardiac wall velocity signals and cardiac wall displacement signals (mechanical activities of the heart generally). The Bornzin et al. device does not identify portions of the accelerometer signal associated with mechanical events of the heart, including for example, the mitral opening or aortic closure.

The present invention provides an apparatus and method for optimizing the cardiac performance by identifying from an accelerometer signal features associated with mechanical events of the heart. The identified features correspond with the R—R intervals of the patient's heart, whereby the features are analyzed and compared for a plurality of preselected timing intervals to thereby determine an optimal timing interval for the cardiac stimulating apparatus at that given time.

SUMMARY OF THE INVENTION

In accordance with the present invention, a cardiac stimulation device is provided which optimizes cardiac performance and is capable of operating in any one of a plurality of pacing modes, including A—A pacing, A-V pacing, or V—V pacing. The cardiac stimulation device includes an accelerometer or heart sound sensor, a microprocessor-based controller, and a pulse generator for stimulating a patient's heart in a preselected pacing mode, all of which are enclosed in an implantable casing. An internal or external cardiac electrogram for identifying R—R intervals of a patient's heart is coupled to the microprocessor based controller. The microprocessor-based controller is coupled to both the accelerometer and the pulse generator for receiving an input from the former and providing control signals to the latter.

The accelerometer generates a waveform or signal having various features corresponding to the mechanical events of a patient's heart. The signal is transmitted to the microprocessor-based controller for analysis. The microprocessor-based controller identifies from the signal preselected features and corresponds these identified features with the R—R interval. The identified features are analyzed and compared over a preselected number of R—R intervals for a plurality of preselected timing intervals. From the comparison, the microprocessor determines which timing interval of the plurality of preselected timing intervals would be an optimum timing interval thereby optimizing cardiac performance.

In the preferred embodiment, each of several mechanical heart events may be associated with separate identified features $f_a$, $f_b$, . . . $f_n$ of the accelerometer signal. For example, features $f_1$ and $f_2$ of the signal identified over a cardiac cycle and measured over an R—R interval may correspond to the first heart sound event $S_1$ and the second heart sound event $S_2$ of the accelerometer signal. A characteristic value for each feature is calculated for each timing interval. The characteristic value may include an average value, a maximum value, a minimum value, or the median value of the feature over a preset time. The characteristic values of the features for the several different timing intervals in the set are analyzed and compared to determine the optimum timing interval of the cardiac stimulation device, which maximizes cardiac performance.

One illustrative example of this analysis follows. The microprocessor-based controller may, for example, calculate the average amplitudes for the first and second heart sound events $S_1$ and $S_2$ in the accelerometer signal over a preset period of complete R—R intervals. The average amplitudes of $S_1$ and $S_2$ are calculated for each timing interval in a set of timing intervals. The average amplitudes for each timing interval of the set are compared to determine which timing interval is associated with the optimum amplitudes of $S_1$ and $S_2$ (either maximum or minimum). This timing interval value is the optimum timing interval at the current time for the specific patient's heart. The cardiac stimulating device is then programmed to automatically adapt or to be set manually to operate at this optimum timing interval. Those skilled in the art will recognize that other features, including the frequency or timing, could likewise be used in the analysis of the accelerometer signal. Also, the features may alternatively be analyzed and compared over a preselected number of respiratory cycles, wherein the microprocessor based controller corresponds the identified features with an R—R interval in a respiratory cycle.

The analysis of each feature of the accelerometer signal preferably occurs when the patient is at rest, the quiescent period. The accelerometer signal may also be used to determine the period of quiescent activity. Analyzing the accelerometer signal during the period of quiescent activity minimizes motion artifact in the accelerometer signal. Further, analyzing the signal during the period of quiescent activity allows the measurements to be taken during relative steady state hemodynamic conditions.

Those skilled in the art will recognize that the accelerometer and other components may be mounted externally, linking these components with the microprocessor by telemetry. However, a single self-contained implantable cardiac stimulating device is preferred.

It is accordingly a principal object of the present invention to provide a cardiac stimulation device capable of dual chamber pacing which includes an accelerometer, wherein the stimulation device optimizes cardiac performance based on an analysis and comparison of features identified from the accelerometer's signal over a plurality of preselected timing intervals.

Another object of the present invention is to provide a cardiac stimulator which maximizes cardiac performance through non-invasive means by analyzing features of a signal transmitted from an accelerometer associated with mechanical events of the heart to thereby determine the optimum timing interval of the cardiac stimulator.

Still another object of the present invention is to provide a method for optimizing cardiac performance by non-intrusively determining the optimal timing interval based on the mechanical performance of the patient's heart.

These and other objects and advantages of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION OF THE PREFERRED EMBODIMENT

Figure 1:
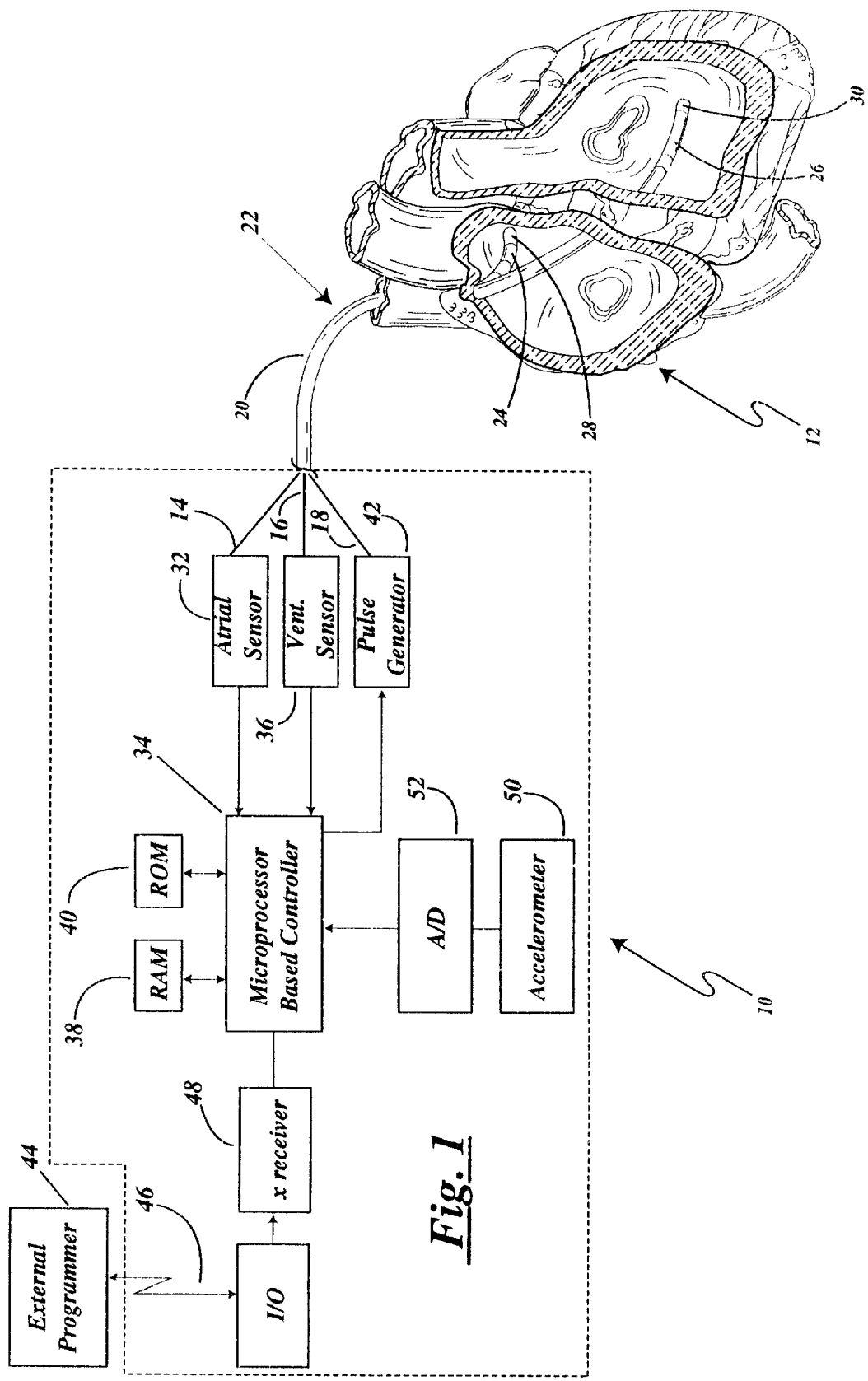
FIG. 1 is a partial sectional perspective view of a patient's heart with a first end of a lead inserted in the patient's heart and a second end of the lead connected to a cardiac stimulator.

Referring first to FIG. 1, there is shown generally in block diagram a cardiac stimulator or dual chamber pacemaker 10

(enclosed by a dotted line) operatively connected to a patient's heart 12 by electrical conductors 14, 16, and 18 embodied in a pacing lead 20. The first end of the pacing lead 22, inserted into the patient's heart 12, branches into an atrial branch 24 and a ventricular branch 26. The atrial branch 24 connects to a first set of stimulating and sensing electrodes 28 which are adapted to be disposed in the right atrium of the heart 12. The right ventricular branch 26 connects to a second set of stimulating and sensing electrodes 30. Those skilled in the art will appreciate that other suitable leads of known construction may alternatively be coupled to the cardiac pacer 10.

The atrial branch 24 of pacing lead 22 is connected by conductor 14 to an atrial sense amplifier 32 which is arranged to sense the occurrence of P-wave activity relating to atrial events. The resulting atrial event signal is then fed to an input of a microprocessor-based controller 34. In a similar fashion, the ventricular branch 26 is operatively coupled by conductor 16 to a ventricular sense amplifier 36. The ventricular sense amplifier 36 functions to detect R-wave activity relating to right ventricular depolarization. The signal representing the R-wave activity is then fed to an input of a microprocessor-based controller 34.

The microprocessor-based controller 34 is programmed to operate in any one of a plurality of pacing modes well known to those skilled in the art including A—A pacing, V—V pacing or A-V pacing. For example, it can pace the atrium and pace either the right ventricle, the left ventricle or both the right and left ventricles when operating in a bi-ventricular mode. The microprocessor-based controller 34 may also sense the atrial event signal and then pace the right, left or both of the ventricles. While FIG. 1 depicts a pacing/sensing lead in the right atrium and right ventricle, those skilled in cardiac rhythm management systems can configure leads for left ventricular and bi-ventricular pacing.

The microprocessor 34 further has both RAM (random access memory) 38, and ROM (read only memory) 40 for storing programs and data, which allows generally: the processing of a signal from an electrogram, identification of features from the signals received by the accelerometer sensor, analyzing and comparing features for a given preset plurality of timing intervals, storing various information derived from the analysis, and changing the preset constants of the program.

The microprocessor 34 controls the cardiac stimulating pulses delivered by pulse generator 42 to one or both of the first and second stimulating electrodes 28 and 30 (depending upon the pacing mode selected). Further, the microprocessor-based controller 34 establishes the optimal timing interval. The timing interval to be optimized may include the timing interval between intrinsic or paced stimulations in preselected chambers of the heart, for any of the following pacing modes: A—A pacing, the V—V pacing and A-V pacing. A timing interval for A—A pacing refers to the timing between the right and left atrial contractions (either intrinsic or paced), a timing interval for V—V pacing refers to the timing between the right and left ventricular contractions (either intrinsic or paced), and a timing interval for A-V pacing refers to the timing between atrial and ventricular contractions (either intrinsic or paced), when sensing/pacing in any one of the following configurations: $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

Cardiac stimulating devices capable of telemetering various status information including selecting a pacing mode and other parameters including the timing interval (determined by the physician), are commercially available from, for example Cardiac Pacemakers, Inc., St. Paul, Minn. An external programmer 44 having a microprocessor and associated memory transmits information in a conventional way through a telemetry link 46 and transmission receiver 48 of the cardiac stimulator's microprocessor. Using the programmer 44 and the telemetry link 46, operating parameter values for the cardiac pacer 10 can be delivered to it by a cardiologist for setting the cardiac cycle pacing parameter values to be utilized, including the timing interval.

An accelerometer 50 may be positioned within the casing of the cardiac stimulator or pacer and coupled to the microprocessor based controller 34 through an analog/digital convertor 52. The casing of the cardiac pacer 10 is implanted in a surgically made pocket, typically in either the left or right shoulder region of the patient. By positioning the accelerometer in the casing (not shown) of the cardiac pacer, the accelerometer 50 generates a global signal associated with various atrial and ventricular events. A globalized signal is preferred over a localized signal (a signal transmitted from an accelerometer in direct contact with an outer wall of the heart). Alternatively, the accelerometer may be attached to the lead 20 to sense atrial and ventricular events. The signal, therein, would resemble a less preferred localized signal.

An analog signal of the accelerometer 50 comprises events associated with heart sounds, compressions, and/or cardiac wall accelerations and decelerations caused from cardiac activity along with motion artifacts and respiratory events. The analog signal is transmitted through the analog/digital converter 52 and then to the microprocessor 34 for analysis. The accelerometer's 50 signal is digitized by the analog/digital converter 52. The digitized signal is signal processed and analyzed to identify various pre-selected features of the signal. The signal from the accelerometer 50 may also be used to evaluate levels of physical activity, thereby identifying periods in which physical activity is low.

Figure 2:
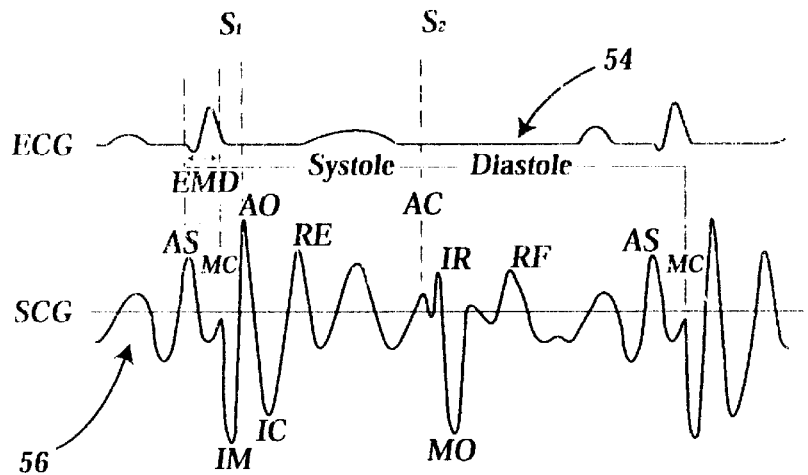
FIG. 2 is a graph showing an exemplary signal received from an electrocardiograph elevated above and aligned timewise, with an exemplary signal received from an accelerometer.

Referring next to FIG. 2, a waveform signal 54 produced from an ECG and an accelerometer signal 56 are shown for reference and comparison. The R—R interval may be identified from the cardiac electrogram 54. The accelerometer signal 56 between successive R waves is likewise represented by a waveform. The waveform has been reported to be associated with various mechanical events of the heart. The waveform events include: Atrial systole (AS), Mitral closure (MC), Isovolumic movement (IM), Aortic opening (AO), Isovolumic contraction (IC), Rapid Ventricular ejection (RE), Aortic closure (AC), Isovolumic relaxation (IR), Mitral Opening (MO), Rapid ventricular filling (RF) and Electromechanical delay (EMD). As previously discussed, the separate mechanical events of the heart may be identified from various features of the waveform corresponding with each event, for example, the amplitude, the timing, or an amplitude in the frequency domain.

The values for various features ($f_a$, $f_o$ . . .) of the accelerometer signal 56 between successive R—R intervals may be selected and analyzed. For example, the feature $f_1$ may be associated with the first heart sound, which is thought to be caused by the closing of the mitral valve and to a lesser extent by the opening of the aortic valve. The feature $f_2$ may be associated with the second heart sound, which is thought to be caused by the closing of the aortic valve and to a lesser extent by the opening of the mitral valve. These two features $f_1$ and $f_2$ may be analyzed either individually or in combination with respect to an independently determined standard hemodynamic cardiac performance parameter.

Figure 3:
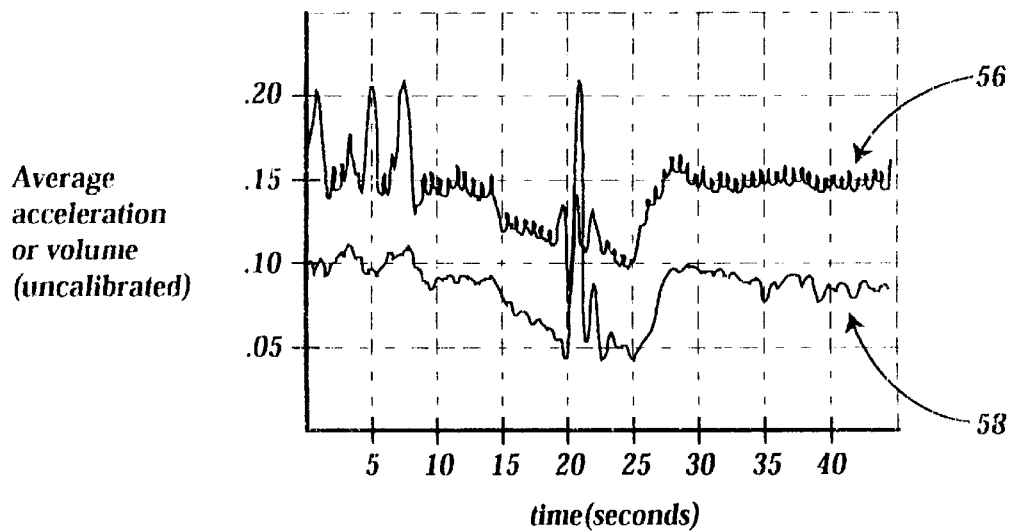
FIG. 3 is a graph for comparing an accelerometer signal to an impedance volume signal.

The significance of the event's features of the accelerometer signal 56 are shown in FIGS. 3–10 and described immediately below. FIG. 3 shows a comparison between a processed accelerometer signal 56 (as measured by an accelerometer positioned externally on the chest) and a left ventricular volume signal 58 (as measured by intraventricular impedance). Each signal 56 and 58 was low pass filtered with a moving average filter having a time constant comparable to a single heartbeat. By filtering the accelerometer signal a specific event feature may be separated out from the waveform. Those skilled in the art will recognize that the signal may alternatively be filtered, integrated, averaged from peak to peak or mean averaged. The signals 56 and 58 were recorded during an Inferior Vena Caval (IVC) occlusion. A trend relationship is shown between the impedance volume 58 and accelerometer 56 signals after similar processing.

Figure 4:
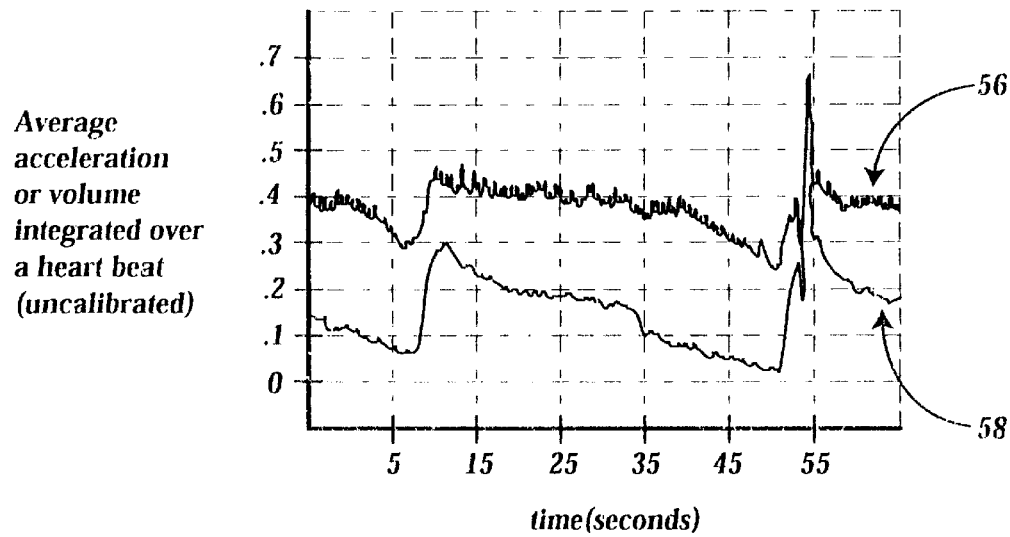
FIG. 4 is another graph for comparing a filtered accelerometer signal to a filtered impedance volume signal.

FIG. 4 shows a plot of a processed accelerometer signal 56 that was high pass filtered, rectified, and low pass filtered and a similarly processed impedance volume signal 58 during the injection of a Dobutamine bolus. The Dobutamine was administered to produce an abrupt and short lived increase in stroke volume. As in FIG. 3, a comparison of the plots shows a trend relationship between the impedance volume 58 and accelerometer 56 signals. Both plots indicate that the accelerometer signals 56 contain information relating to the mechanical events (in this case volume) of the heart.

Figure 5:
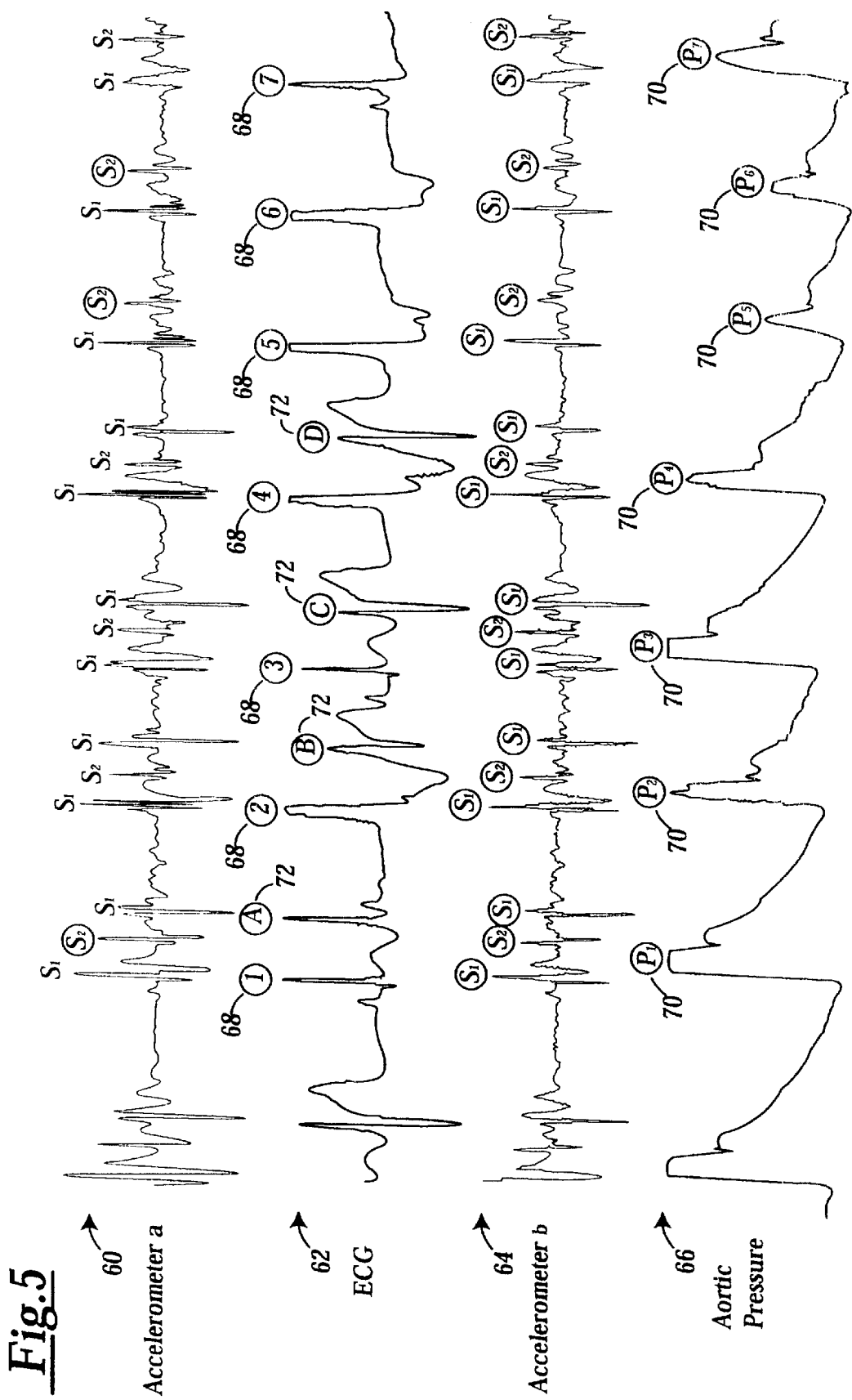
FIG. 5 is a graph showing two distinct accelerometer signals with corresponding ECG and aortic pressure signals.

Referring next to FIG. 5, signals received simultaneously associated with an accelerometer-a 60, cardiac electrogram or ECG 62, accelerometer-b 64, and aortic pressure 66 are shown for comparison. The signals 60–66 were sensed over several R—R intervals, while the pacing rate was changed from one pacing rate to another, higher, pacing rate. Accelerometer-a and accelerometer-b were positioned independently relative to the patient's heart. The signals 60 and 64 received from accelerometer-a and accelerometer-b depict similar information. Hence, the information contained in an accelerometer signal 56 is approximately independent of the accelerometer's 50 position.

From FIG. 5 it can be seen that some ECG 62 R wave events (either intrinsic or paced) 68 result in aortic ejection and therefore have an associated aortic pressure pulse 70. These ejection R wave events 68 are labeled 1, 2, . . . 7, and the resulting aortic pressure pulse events 70 are labeled $P_1, \ldots, P_7$. There are other ECG 62 R wave events which do not lead to aortic ejection and therefore do not have associated pressure pulses. These non-ejection R wave events 72 are labeled A, B, C, and D. For each ejection R wave event 68 (1, . . . , 7) and each non-ejection R wave event 72 (A, B, C, D) an accelerometer event $S_1$ (associated with the first heart sound) results. Note, however, that only the ejection R wave events 68 (1, 2, . . . , 7) result in an accelerometer event $S_2$ (associated with the second heart sound). A comparison of signals shows a definite correlation among the ECG events, the accelerometer events, and the aortic pressure events.

An analysis of the graphs shows that both the amplitude of the $S_2$ event of the signals from accelerometer-a and accelerometer-b and the mean aortic and pulse pressures of the $P_1$ aortic pressure event are greatest during the ECG 62 R wave event 1. Likewise, an analysis of the graphs shows that both the amplitude of the $S_2$ event of the signals from accelerometer-a and accelerometer-b and the mean aortic and pulse pressures of the $P_5$ and $P_6$ aortic pressure events are smallest during the ECG 62 R wave events 5 and 6. Therefore, it is believed that the change in amplitude of the $S_2$ event of an accelerometer signal correlates with the change in mean aortic and pulse pressures. Thus, the accelerometer signals contain information relating to the mechanical function of the heart and to standard hemodynamic/cardiac performance parameters, and therefore may be used independently to optimize cardiac performance.

Figure 6:
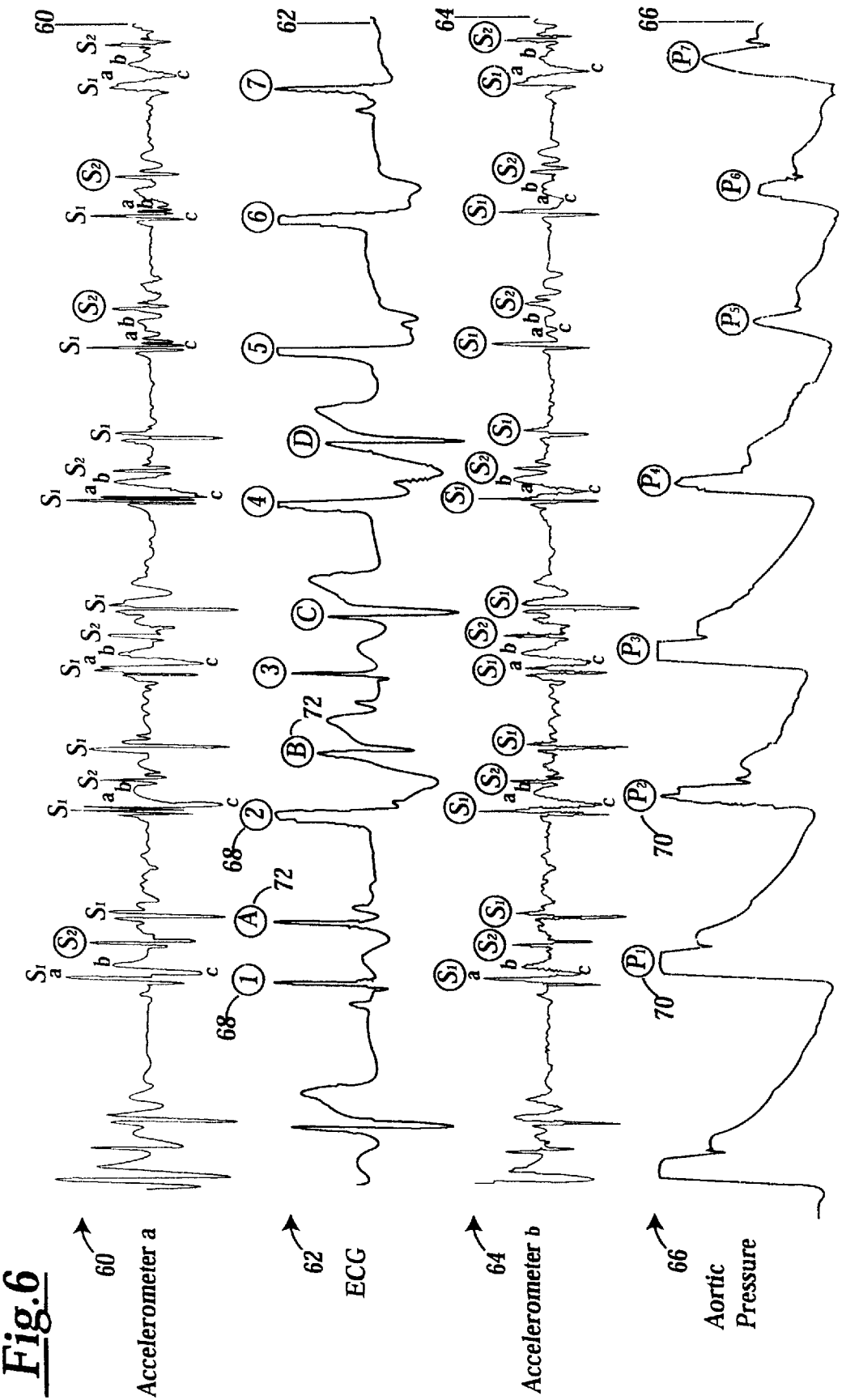
FIG. 6 is a graph showing two distinct accelerometer signals with corresponding ECG and aortic pressure signals.

Referring now to FIG. 6, the accelerometer signals of FIG. 5 are further labeled with "a", "b", and "c". These abc events occur during the ejection period, and the amplitude of the "abc" event appears to be correlated with the magnitude of the pulse pressure and aortic pressure events. An analysis of the graphs shows that the amplitude of the abc component of the signals from accelerometer-a and accelerometer-b and the mean aortic and pulse pressures of the $P_1$ aortic pressure event are greatest during the ECG 62 R wave event 1. Likewise, an analysis of the graphs shows that the amplitude of the abc component of the signals from accelerometer-a and accelerometer-b and the mean aortic and pulse pressures of the $P_5$ and $P_6$ aortic pressure events are smallest during the ECG 62 R wave events 5 and 6. In addition, all of the amplitudes of the abc components are approximately monitonically related to the associated aortic pressure event values. Thus the amplitude of the abc component is correlated with the aortic and pulse pressure event values. Again, the accelerometer signals contain information relating to the mechanical function of the heart and to standard hemodynamic/cardiac performance parameters, which may be used independent of an ECG or aortic pressure sensor to optimize cardiac performance.

Referring to FIGS. 7–10, the graphs show characteristic values of predetermined features of the accelerometer signal 56 as a function of the A-V interval. The graph shown in FIG. 7 demonstrates the characteristic value $<f_1>$ of the feature $f_1$ associated with the first heart sound event $S_1$ as a function of the A-V interval during $A_R$-$V_R$ pacing.

The accelerometer signal 56 was measured over a period of three minutes from a DDD pacemaker positioned in a left PG pocket. Near the end of the three minute period, a value for $f_1$ was determined for each R—R interval by calculating the difference between the maximum value of the waveform and the minimum value of the waveform in the region associated with $S_1$ (the first heart sound). The characteristic value for the feature, $<f_1>$, at the particular A-V interval was the largest (maximum) value of $f_1$ over the predetermined time interval (one complete respiration cycle near the end of a three minute period). The $<f_1>$ values were determined for the A-V intervals (timing intervals) of 75 ms, 100 ms, 125 ms, 150 ms, 175 ms, and 200 ms. Those skilled in the art will recognize that the average value, the maximum value, the minimum value or the median value may be used to determine the characteristic value for each feature $f_a$. . . $f_b$.

Figure 7:
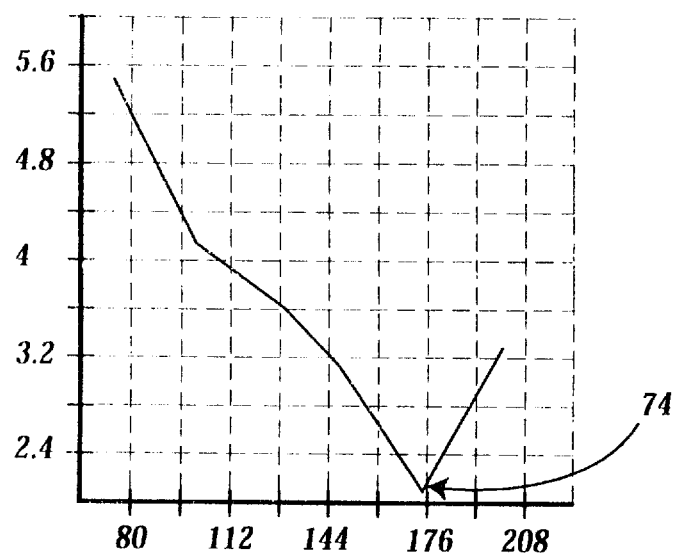
FIG. 7 is a graph showing the characteristic value $<f_1>$ of an accelerometer signal (measured from the left shoulder region) as a function of the A-V interval.

The result, as indicated in FIG. 7, is that the minimum $<f_1>$ 74 occurred at an A-V interval of 175 ms. This minimum of $<f_1>$ is associated with the optimum A-V interval (optimum timing interval for $A_R$-$V_R$ pacing) for the particular patient under observation. The accuracy of this result was verified by determining that the average stroke distance as a function of the A-V interval, determined simultaneously from continuous wave Doppler, has a maximum value at 175 ms. Since stroke distance is a standard hemodynamic/cardiac performance parameter, A-V interval=175 ms is the optimum A-V interval. Hence, the optimum A-V interval may be determined by analyzing an accelerometer signal and determining the minimum value 74 of $<f_1>$.

Figure 8:
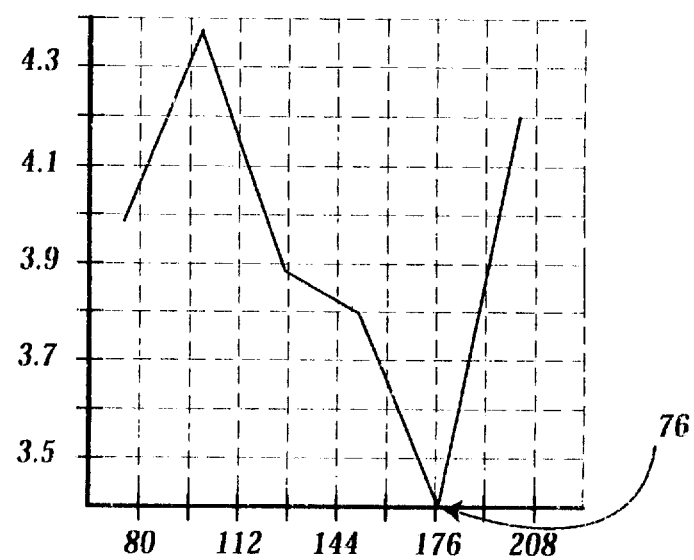
FIG. 8 is a graph showing the characteristic value $<f_2>$ of an accelerometer signal (measured from the left shoulder region) as a function of the A-V interval.

Likewise, as indicated in FIG. 8, the accelerometer signal 56 was analyzed to determine the characteristic value $<f_2>$ of the feature $f_2$, associated with the second heart sound event $S_2$, during the same R—R intervals. The minimum value 76 for $<f_2>$ occurs at the same optimum A-V interval. Thus, $<f_2>$ also has its minimum value at the optimum A-V interval.

Figure 9:
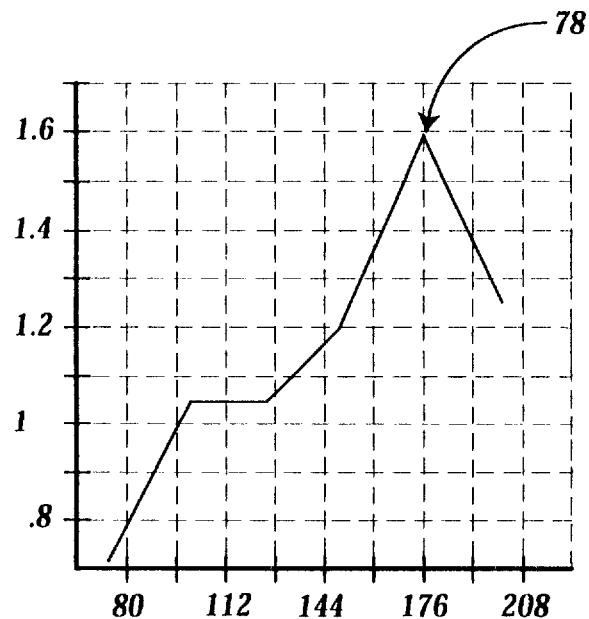
FIG. 9 is a graph showing $<f_2>/<f_1>$ (the characteristic value $<f_2>$ divided by the characteristic value $<f_1>$ of an accelerometer signal measured from the left shoulder region) over the set of A-V intervals.
Figure 10:
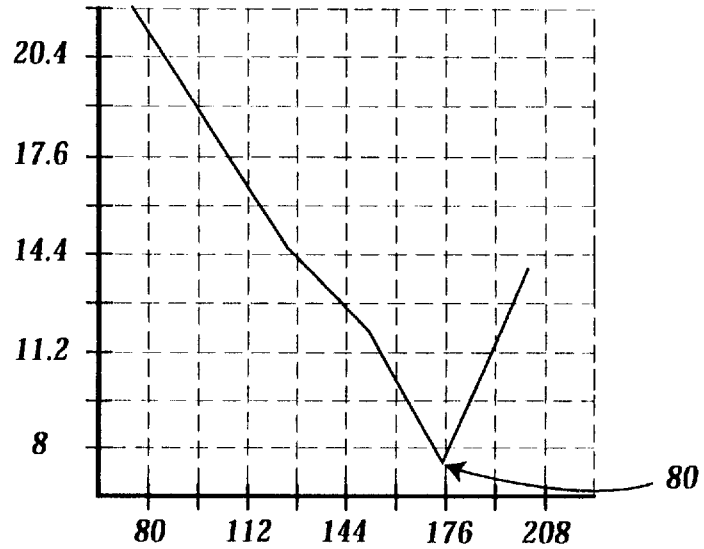
FIG. 10 is a graph showing $<f_2>*<f_1>$ (the characteristic value $<f_2>$ multiplied by the characteristic value $<f_1>$ of an accelerometer signal measured from the left shoulder region) over the set of A-V intervals.

FIG. 9 shows a graph representing $<f_2>$ divided by $<f_1>$ as a function of the A-V interval. The maximum value 78 for $<f_2>/<f_1>$ occurs at the same optimum A-V interval. FIG. 10 is a graph showing $<f_2>*<f_1>$ as a function of the A-V interval. The minimum value 80 of $<f_2>*<f_1>$ occurs at the same optimum A-V interval. Hence, an analysis and comparison of the features of the accelerometer signal may be used to determine the optimal A-V interval.

FIGS. 9 and 10 illustrate that an accelerometer's feature (such as $<f_2>/<f_1>$) used to determine the optimum A-V interval may actually be defined in terms of the characteristic values of other features. In addition, any accelerometer feature used to determine the optimum A-V interval may actually be defined in terms of weighted characteristic values of other features, such as $W_1*<f_1>+W_2*<f_2>$, where $W_1$ and $W_2$ are constants. FIGS. 7–10 indicate that each of the four characteristic values $<f_1>$, $<f_2>$, $<f_1>*<f_2>$, and $<f_2>/<f_1>$ has a maximum or minimum which occurs at the same, optimum A-V interval, so that only a determination of one of the four is needed to determine the optimum A-V interval. In general, however, this may not be the case. In practice, the features of two or more accelerometer events may need to be analyzed in order to determine an optimum timing interval, thereby requiring a multidimensional feature analysis.

Figure 11:
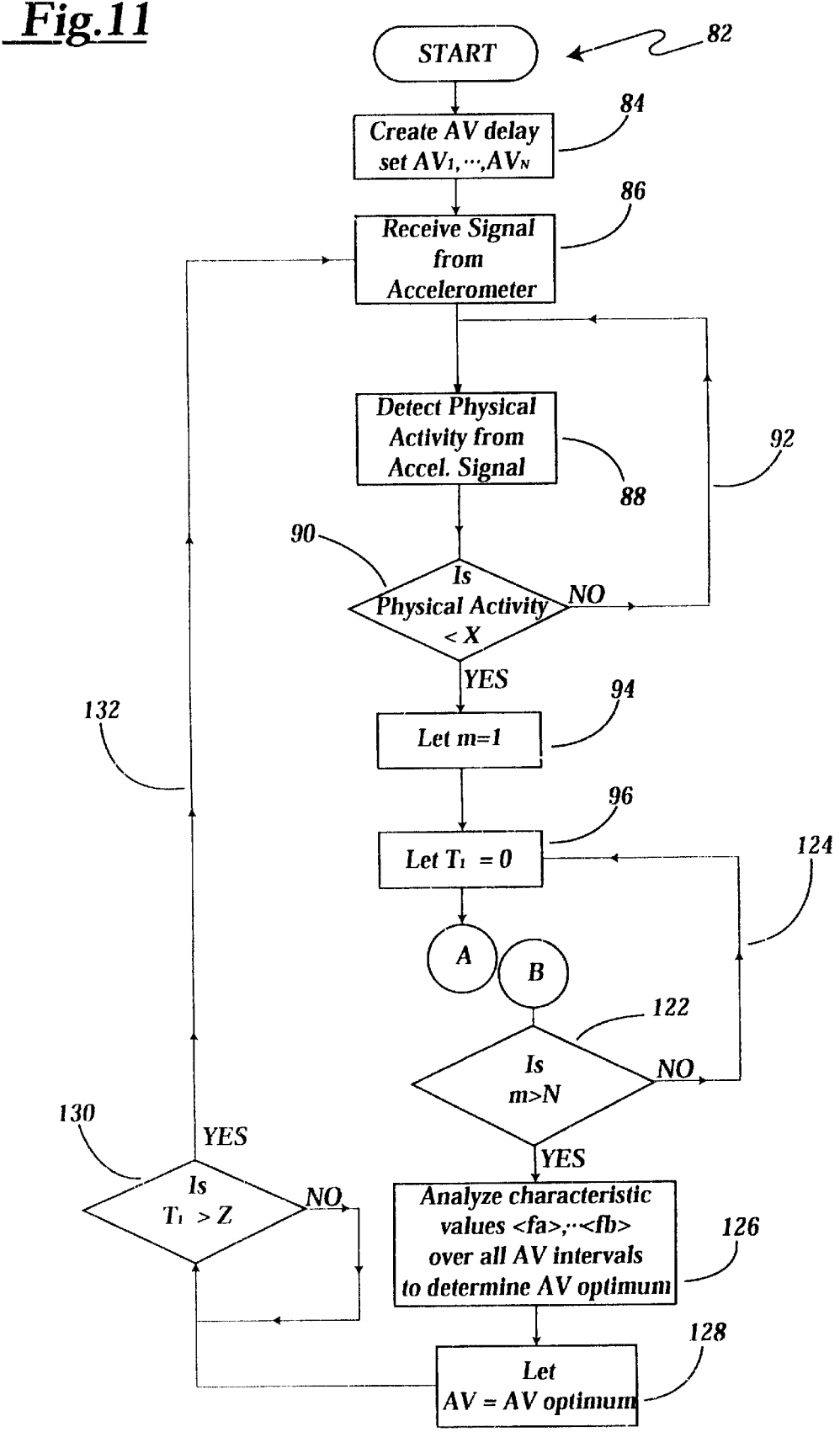
FIGS. 11 and 12, together, comprise a flow diagram of the software used to run the microprocessor based controller to determine the optimum timing interval to thereby optimize cardiac performance.
Figure 12:
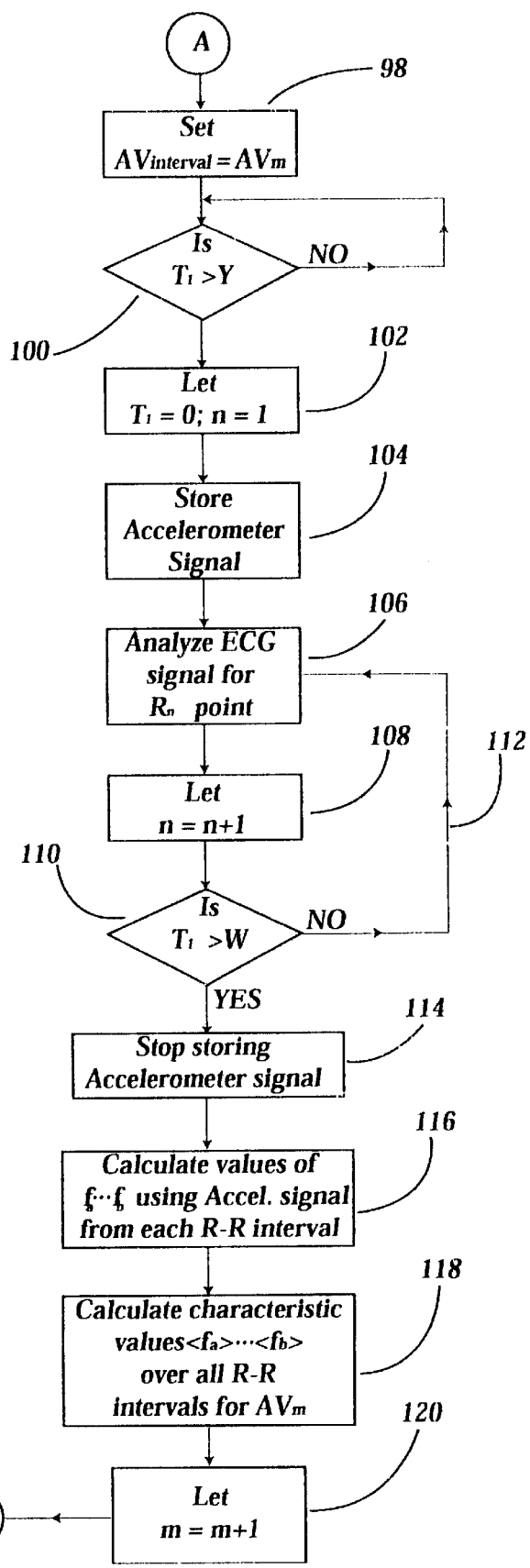

In further explaining the invention, and especially the flow chart of FIGS. 11 and 12, it is assumed that the timing interval of the cardiac stimulation device that is periodically changed is the atrial-ventricular (A-V) interval. It should be emphasized that the invention is not to be limited to use in a system where only the A-V delay interval is adjusted, and the results of the adjustment on physiologic parameters noted. Those skilled in the art will recognize that the algorithm described equally applies to optimizing other timing intervals for any of a number of pacing modes. For example, the lower rate limit interval (R—R), the interval between right and left atrial stimulations ($A_R$-$A_L$ interval), the interval between right and left ventricular stimulations ($V_R$-$V_L$ interval), $A_R$-$V_R$ interval, $A_L$-$V_R$ interval, $A_R$-$V_{RL}$ interval, $A_L$-$V_{RL}$ interval, $A_L$-$V_L$ interval etc. may be subjected to periodic changes with the effects on the body of such changes being noted and stored.

The algorithm 82 used to determine the optimum A-V interval is shown. An ordered set of pre-set A-V interval values is programmed into the device at the time of implant by the physician (block 84). This timing interval set contains a range of A-V interval values over which the unit will automatically switch. Oftentimes, the sequence of the set will comprise alternation between a baseline without pacing and a randomly selected A-V interval. This alternation reduces hysteresis and other effects that a previous A-V interval value may have on the next A-V interval.

The values within the set are ordered by an A-V interval index m (see also block 98), which ranges from m=1 to N, where N is the total number of A-V intervals to be investigated. A particular A-V interval in the set may in actuality be a specification for using the patient's baseline rhythm. This baseline rhythm could be unpaced (intrinsic) or paced (at an A-V interval somewhat less than the intrinsic A-V interval). One reason for using a baseline rhythm immediately preceding each paced A-V interval is to ensure that each paced A-V interval starts with the same conditions, i.e., the current baseline state. In addition, the determination of the optimum A-V interval could involve a comparison of feature values of the paced A-V interval with feature values of the immediately preceding baseline rhythm.

Those skilled in the art will recognize that the algorithm identified in FIGS. 11 and 12 may be repeated continuously or repeated at periodic intervals. At any time, the operator may change the default setting by entering programmable parameters and transmitting these changes through the remote programmer 44 and transceiver 48.

Referring next to block 86, the microprocessor receives a digitized accelerometer signal 56 from the accelerometer 50. A portion of this signal 56 represents the level of physical activity of the patient. The detection of physical activity from the accelerometer signal is represented by block 88. An initial test is made at decision block 90 to determine whether the physical activity is less than a predetermined amount X, which is indicative of a patient at rest. If the physical activity is greater than the predetermined amount X, the physical activity is detected and analyzed until the physical activity drops below X (see loop 92). Typically, the ratio of the accelerometer signal amplitude for one in motion to one at rest is on the order of a magnitude of ten. When the patient is resting, the accelerometer readings are less subject to noise and motion artifacts.

When the physical activity is less than the predetermined amount X, the A-V interval index m is then set to 1 (block 94). A timer $T_1$ is then started, setting $T_1=0$ (see block 96) and a series of steps shown in FIG. 12 are then made whereby the A-V interval is periodically changed to determine which A-V interval is associated with the optimum accelerometer feature value.

More specifically, the A-V interval is set to the current A-V interval setting A-$V_m$ (block 98) and remains at the setting for a preprogrammed period of time Y (see decision block 100). The timer, $T_1$, is then reset to 0, and the R wave index n is set to 1 (block 102). The microprocessor 34 stores the accelerometer signal 56 (block 104). Simultaneously, the microprocessor 34 analyzes the electrogram signal 54 and determines the point in the signal that is associated with the depolarization of ventricles (the nth R wave, $R_n$; see block 106). The R wave index n is incremented (block 108). The microprocessor continues determining R waves and storing the accelerometer signal for a predetermined interval w, which is a predetermined period of time or a predetermined integer number of complete respiratory cycles (see decision block 110). The microprocessor continues to determine the R-waves and stores the accelerometer signal in association with the determined R-waves (see loop 112).

After the programmed interval w, accelerometer signal 56 storage stops (block 114). The value for each selected accelerometer feature $f_a$, $f_b$, . . . of the signal for each R—R interval is calculated (see block 116). The characteristic value of each feature $<f_a>$, $<f_b>$, . . . is calculated over all the R—R intervals determined in block 106 and then stored (block 118), in association with the current A-V interval setting A-$V_m$. Thus the characteristic value is determined over all the complete R—R intervals occurring within the predetermined interval w. The A-V interval index m is then incremented (block 120); thereafter, a decision is made whether all of the N different A-V intervals in the set have been tested (block 122 in FIG. 11). If the incremented A-V interval index m does not exceed N, the largest A-V interval index, the microprocessor continues the analysis of the accelerometer signal using $AV_m$, the A-V interval value assigned to the incremented index setting (see loop 124).

After all the accelerometer signals 56 for the various A-V intervals have been analyzed, all the characteristic values for each feature $<f_a>$, $<f_b>$, . . . associated with all the A-V intervals are then analyzed to determine the optimum A-V interval value (see block 126). The calculation and analysis of each feature $<f_a>$, $<f_b>$, . . . may be consistent with that described above. If the ordered set of A-V interval values (block 84) are such that an actual paced A-V interval is immediately preceded by a paced or unpaced baseline rhythm, then the determination of the optimum A-V interval could involve a comparison of feature values of the paced A-V interval rhythm with feature values of the immediately preceding baseline rhythm.

The A-V interval setting is then set to the optimum A-V interval value (A-$V_{optimum}$) at block 128. PG pacing utilizes this A-$V_{optimum}$. The A-V interval remains at the A-$V_{optimum}$ until a predetermined time period Z has passed (block 130). The analysis is then repeated via loop 132 to determine a new optimum A-V interval.

Those skilled in the art will recognize that the optimum A-V interval value may be determined over a specified period of time. They will also recognize that this algorithm 82 may be used to determine the optimal A-V interval setting when the patient is not at rest. The optimization of the A-V interval is especially useful to CHF patients.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac stimulating apparatus functioning in a preset pacing mode, and programmed to optimize cardiac performance of a patient's heart, comprising:
   a) a dual chamber cardiac pacer and leads coupled to said cardiac pacer for sensing atrial and ventricular events of a patient's heart and for stimulating preselected chambers of the heart, and further including a cardiac cycle means for identifying cardiac cycles of the patient's heart;
   b) a cardiac electrogram coupled to said cardiac pacer for identifying R—R intervals of the patient's heart;
   c) an accelerometer contained within a housing of said cardiac pacer and coupled to a microprocessor based controller of said cardiac pacer, said accelerometer having a filter wherein said accelerometer transmits to the cardiac pacer a waveform having various features associated with mechanical movement events within an atrium and mechanical movement events within a ventricle; and
   d) said microprocessor based controller including feature means for identifying pre-selected features of the waveform transmitted by the accelerometer, means for corresponding the R—R interval identified by the cardiac electrogram with the features identified by the feature means, and analyzing means for analyzing identified features over corresponding R—R intervals, wherein the identified features are analyzed and compared by said microprocessor over a preselected number of R—R intervals for a plurality of preselected timing intervals, said timing intervals being a time between at least one of intrinsic and paced stimulations of pre-selected chambers of the heart, to thereby determine an optimum timing interval.

2. The cardiac stimulating apparatus as recited in claim 1 wherein said pre-selected features are selected from the group consisting of an amplitude in the frequency domain of the waveform, an amplitude associated with a first heart sound and an amplitude associated with a second heart sound.

3. The cardiac stimulating apparatus as recited in claim 1, wherein said microprocessor-based controller analyzes and compares characteristic values of the identified features over the plurality of pre-selected timing intervals.

4. The cardiac stimulating apparatus as recited in claim 1, wherein said microprocessor-based controller includes a means for identifying, from the waveform transmitted by the accelerometer, a time of physical inactivity.

5. The cardiac stimulating apparatus as recited in claim 1, further including a respiratory means for identifying complete respiratory cycles and means for corresponding identified respiratory cycles with the features identified by the feature means, whereby the identified features are analyzed and compared over a plurality respiratory cycles.

6. The cardiac stimulating apparatus as recited in claim 1, wherein the dual chamber cardiac pacer functions in a pacing mode selected from the group consisting of A-V pacing, V—V pacing and A—A pacing.

7. The cardiac stimulating apparatus as recited in claim 6, wherein the A-V pacing mode is selected from the group consisting of $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

8. A cardiac stimulating apparatus functioning in a rate adaptive preset pacing mode, and programmed to optimize cardiac performance of a patient's heart, comprising:
   a) a dual chamber cardiac pacer and leads coupled to said cardiac pacer for sensing atrial and ventricular events of a patient's heart and for stimulating preselected chambers of the heart, and further including a cardiac cycle means for identifying cardiac cycles of the patient's heart;
   b) a cardiac electrogram coupled to said cardiac pacer for identifying R—R intervals of the patient's heart;
   c) an accelerometer contained within a housing of said cardiac pacer and coupled to a microprocessor based controller of said cardiac pacer, said accelerometer having a filter wherein said accelerometer transmits to the cardiac pacer a waveform having various features associated with mechanical movement events within an atrium and mechanical movement events within a ventricle; and
   d) said microprocessor based controller including feature means for identifying pre-selected features of the waveform transmitted by the accelerometer, respiratory means coupled to said cardiac pacer for identifying complete respiratory cycles, means for corresponding both the R—R interval identified by the cardiac electrogram and the respiratory cycles identified by the respiratory means with the features identified by the feature means, and analyzing means for analyzing identified features over corresponding R—R intervals and respiratory cycles, wherein the identified features are analyzed and compared by said microprocessor over a preselected number of at least one of R—R intervals and respiratory cycles for a plurality of pre-selected timing intervals, said timing intervals being a time between at least one of intrinsic and paced stimulations of pre-selected chambers of the heart, to thereby determine an optimum timing interval.

9. The cardiac stimulating apparatus as recited in claim 8, wherein said pre-selected features are selected from the group consisting of an amplitude in the frequency domain of the waveform, an amplitude associated with a first heart sound and an amplitude associated with a second heart sound.

10. The cardiac stimulating apparatus as recited in claim 8, wherein said microprocessor-based controller analyzes and compares characteristic values of the identified features over the plurality of pre-selected timing intervals.

11. The cardiac stimulating apparatus as recited in claim 8, wherein said microprocessor-based controller includes a means for identifying, from the waveform transmitted by the accelerometer, a time of physical inactivity.

12. The cardiac stimulating apparatus as recited in claim 8, wherein the dual chamber cardiac pacer functions in a pacing mode selected from the group consisting of A-V pacing, V—V pacing and A—A pacing.

13. The cardiac stimulating apparatus as recited in claim 12, wherein the A-V pacing mode is selected from the group consisting of $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

14. A method for optimizing the timing interval of an implantable cardiac pacer between intrinsic and paced stimulations of pre-selected chambers of a patient's heart, said pacer being of the type having a microprocessor-based controller having memory, a pulse generator, and an accelerometer for sensing mechanical atrial and ventricular events contained therein, said method comprising the steps of:

a) pacing a patient's heart with the implantable cardiac pacer, wherein the cardiac pacer has a preset pacing mode, identifies cardiac cycles of the patient's heart and controls a timing interval between at least one of intrinsic and paced stimulations of preselected chambers of the heart;

b) setting the timing interval of the implantable cardiac pacer to a first value of a predetermined set of timing interval values;

c) receiving a signal from the accelerometer;

d) coupling a cardiac electrogram to the implantable cardiac pacer to identify R—R intervals of the patient's heart;

e) identifying pre-selected features from the signal, and storing data associated with identified features of the signal received from the accelerometer for a plurality of R—R intervals in the memory of the microprocessor-based controller;

f) calculating from the identified features, characteristic values of the identified features of the signal;

g) selecting a new timing interval value from the predetermined set of timing interval values;

h) repeating steps c-g until all the timing interval values of the predetermined set of timing interval values have been used;

i) analyzing and comparing the calculated characteristic values for each timing interval value of the predetermined set of timing interval values, to determine an optimum timing interval value; and j) setting the timing interval of the implantable cardiac pacer to the determined optimum timing interval value.

15. The method as in claim 14, and further including, before step b), the further step of inhibiting the steps of b)-j) if a level of physical activity of the patient determined from the signal received from the accelerometer is greater than a predetermined amount.

16. The method as in claim 14 and further including the step of waiting a predetermined amount of time between steps b) and c).

17. The method as in claim 14, further including the step of selecting a pacing mode of the implantable cardiac pacer from a group consisting of A-V pacing, V—V pacing and A—A pacing.

18. The method as recited in claim 17, further including the step of selecting the A-V pacing mode from the group consisting of $A_R$-$V_R$ pacing, $A_R$-$V_L$ pacing, $A_L$-$V_R$ pacing, $A_R$-$V_{RL}$ pacing, $A_L$-$V_{RL}$ pacing, and $A_L$-$V_L$ pacing.

19. The method as recited in claim 14, wherein the pre-selected features are selected from the group consisting of an amplitude in the frequency domain of the waveform, an amplitude associated with a first heart sound and an amplitude associated with a second heart sound.

20. The method as recited in claim 14, wherein the predetermined set of timing interval values comprise alternation between a baseline value and a randomly selected timing interval value.

* * * * *